United States Patent [19]

Haber et al.

[11] Patent Number: 4,813,935
[45] Date of Patent: Mar. 21, 1989

[54] URINARY CATHETER

[75] Inventors: Terry M. Haber, Lake Forest; John A. Lewis, Costa Mesa; Clark B. Foster, Laguna Niguel, all of Calif.

[73] Assignee: Habley Medical Technology Corporation, Laguna Hills, Calif.

[21] Appl. No.: 78,103

[22] Filed: Jul. 27, 1987

[51] Int. Cl.$^4$ .............................................. A61B 25/00
[52] U.S. Cl. ...................................... 604/99; 604/103; 604/246
[58] Field of Search ................................. 604/96–104, 604/53, 54, 246, 247, 250, 256, 264, 265, 266; 251/5; 128/398

[56] References Cited

U.S. PATENT DOCUMENTS

| 3,807,408 | 4/1974 | Summers | 604/104 |
|---|---|---|---|
| 3,970,090 | 7/1976 | Loiacono | 604/104 |
| 4,441,495 | 4/1984 | Hicswa | 604/103 |
| 4,553,959 | 11/1985 | Hickey et al. | 604/247 X |
| 4,571,241 | 2/1986 | Christopher | 604/247 |
| 4,587,954 | 5/1986 | Haber | 604/247 |
| 4,598,707 | 7/1986 | Agdanowski et al. | 604/99 X |

Primary Examiner—Stephen C. Pellegrino
Attorney, Agent, or Firm—Morland C. Fischer

[57] ABSTRACT

An improved urinary catheter having a unique, low volume device by which to retain the catheter within the bladder, so that urine can be removed therefrom. The retaining device consumes less volume in the bladder than that which would ordinarily be consumed by a conventional Foley-style balloon, whereby both the frequency and severity of urinary bladder spasms, which are induced by pressure against the trigonal area of the bladder, can be reduced. What is more, the retaining device is advantageously adapted to provide little resistance, and thereby minimize any damage to the urinary tract, in the event that a patient should suddenly and forceably attempt to remove the catheter from his bladder.

20 Claims, 6 Drawing Sheets

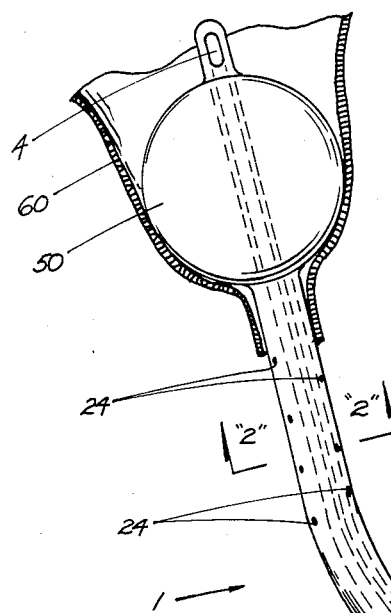
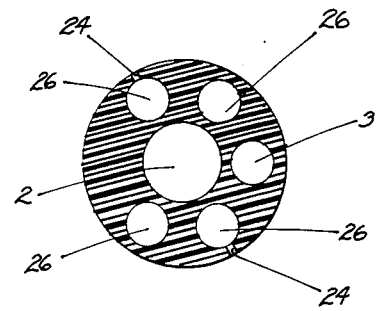
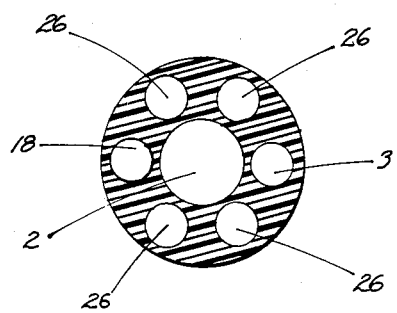
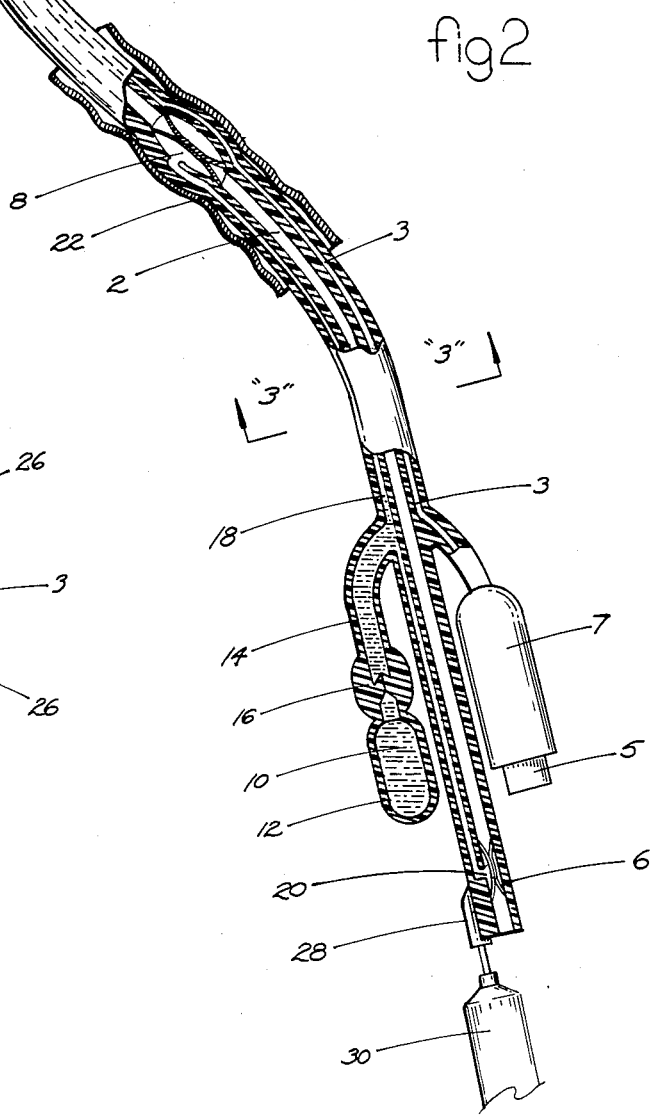
fig1
fig2
fig3

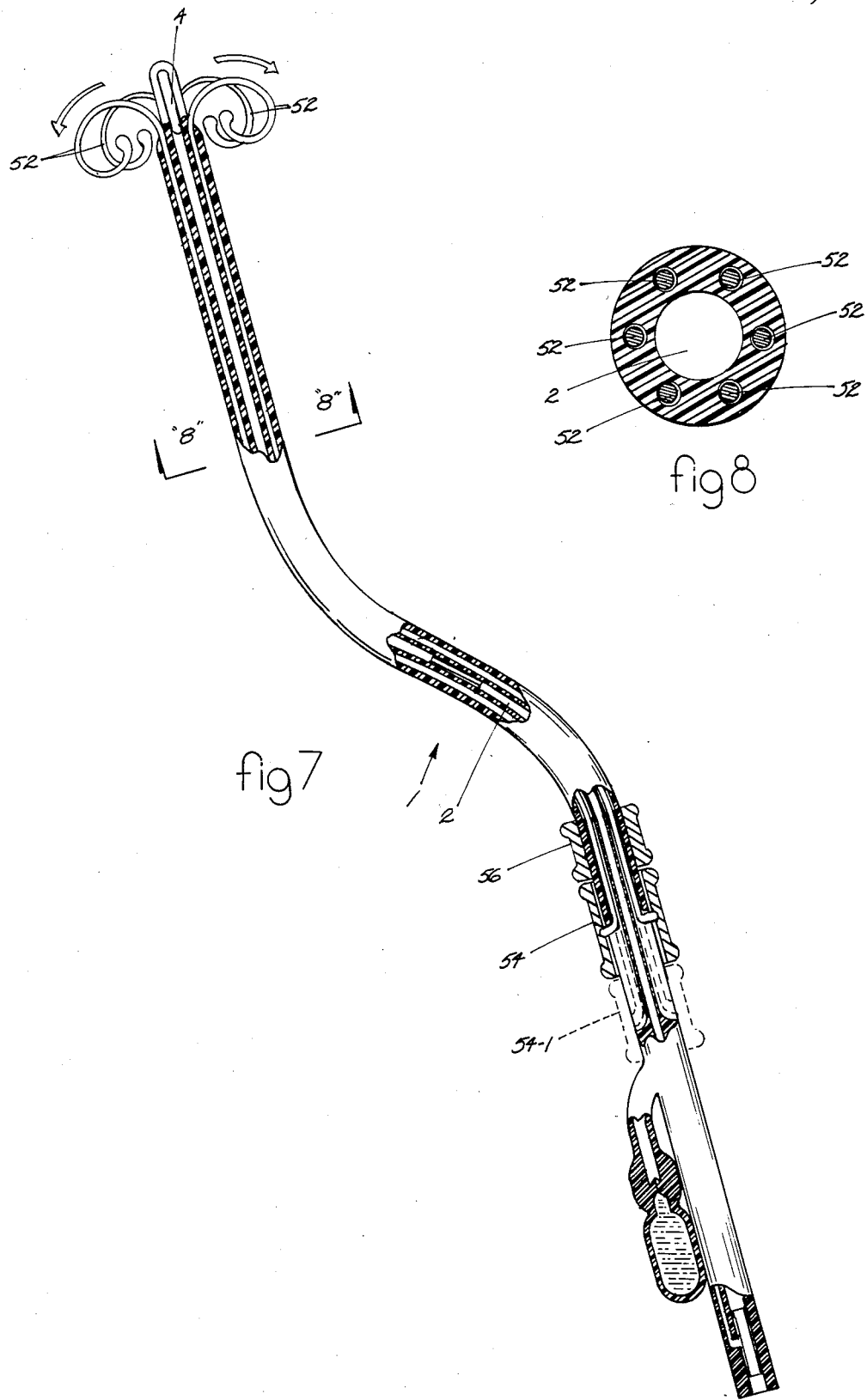

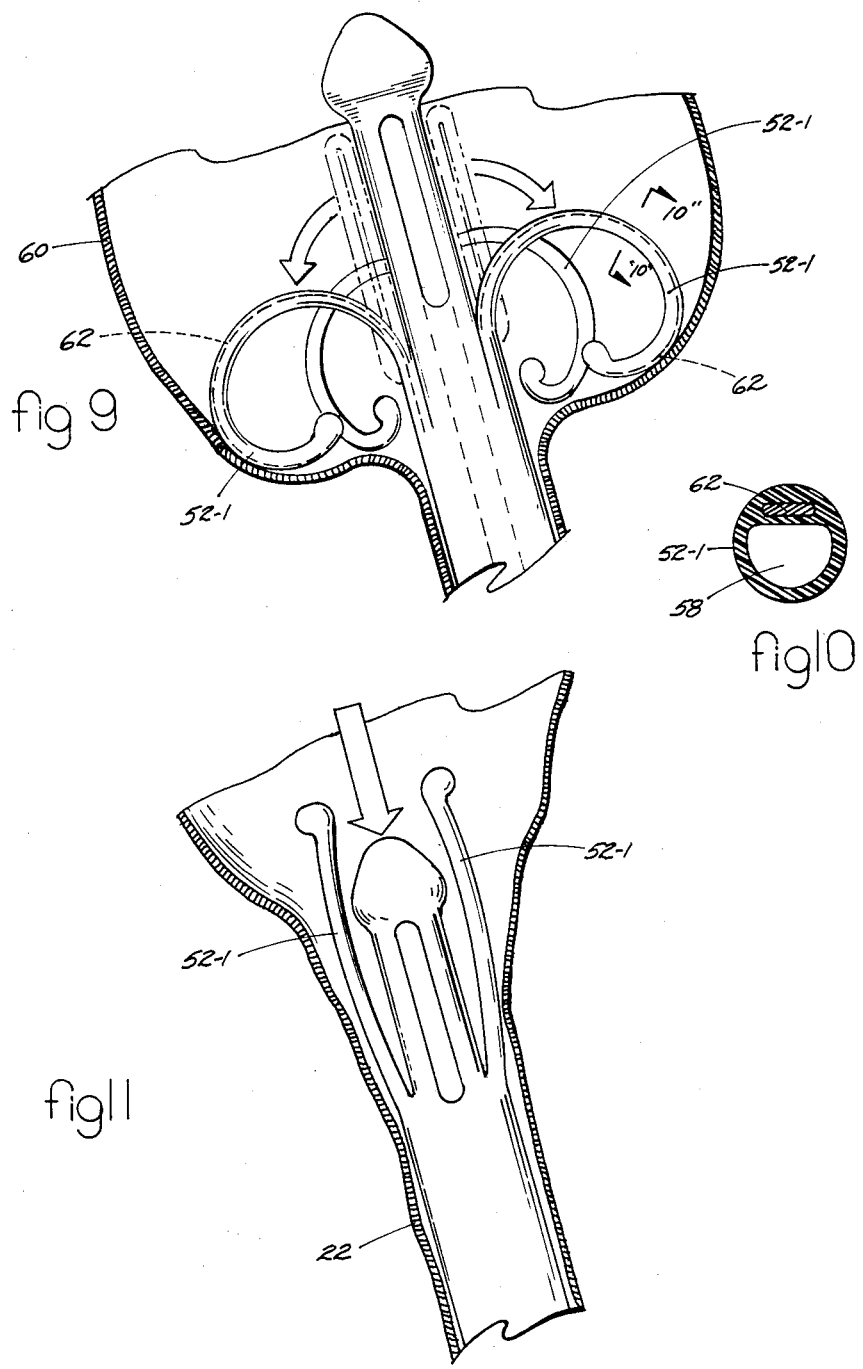

URINARY CATHETER

BACKGROUND OF THE INVENTION

1. Field of the Invention

This invention relates to an improved urinary catheter having a unique, low profile, low volume consuming means by which to retain the catheter within the bladder so that urine can be removed therefrom.

2. Prior Art

As will be known to those skilled in the art, a conventional Foley catheter is inserted into the penis and through the urinary tract of a male patient until the proximal end of the catheter contacts the upper wall of the patient's bladder. The Foley catheter balloon is then inflated, while in situ, and the catheter is retracted slowly until the inflated balloon encounters some resistance against the lower bladder wall. The inflated balloon retains the catheter within the bladder so that urine can be removed therefrom and delivered to a bladder bag for disposal.

However, there are several significant problems which may arise as a consequence of using a conventional Foley catheter. More particularly, an inflated Foley balloon typically assumes a spherical configuration which consumes a relatively large volume within the patient's bladder. The large volume consumed by the Foley balloon correspondingly increases the pressure on the trigonal area of the bladder. The application of excessive pressure against the trigone induces frequent urinary bladder spasms which, in turn, creates a feeling within the patient to urinate. This feeling may make the patient uncomfortable or worry and suggest a condition of urgency when, in fact, no such urgency exists.

Moreover, some patients, especially geriatric males, may suddenly and forceably attempt to jerk out their catheter before the Foley balloon can be deflated. The relatively large resistance which would be encountered by pulling an inflated Foley balloon through the urinary tract has been known to cause significant damage to the prostate, urethra, and sphincteric tissues, thereby resulting in possible hematoma formation, fissuring, sepsis, and, in some cases, even death, in the event that the patient should remove the catheter with the Foley balloon remaining in the inflated condition.

What is still more, the conventional Foley catheter has no means to selectively occlude the central urine passage thereof. Therefore, that is no way to temporarily interrupt the flow of urine through the catheter. Likewise, there is no way to inhibit to ascent of infection up the catheter and into the bladder.

SUMMARY OF THE INVENTION

Briefly, an improved urinary catheter is disclosed by which to overcome the shortcomings of the Foley catheter. The catheter includes a low volume, low profile means by which to retain the catheter within the bladder so that urine may be removed therefrom. More particularly, the retaining means of the improved catheter consumes less volume in the bladder than that which would ordinarily be consumed by a conventional spherically shaped Foley balloon. Accordingly, both the frequency and severity of urinary bladder spasms, as commonly induced by the application of excessive pressure, such as that generated when a Foley balloon engages the trigonal area of the bladder, can be reduced. Thus, by eliminating the application of such pressure against the trigone, the patient will be less likely to experience a feeling of urgency, when, in fact, no such urgency exists.

What is more, the catheter retaining means is adapted to provide little resistance in the event that the patient should suddenly and forceably jerk the catheter out of his bladder. That is to say, the retaining device will automatically conform to the dimensions of the urethra and thereby not oppose a removal of the catheter. In this manner, the urinary tract of the patient will be subjected to minimal trauma and experience less damage.

According to one embodiment of the invention, the retaining means is an inflatable balloon having a torroidal (rather than a spherical) configuration. The balloon may be separated from the catheter in the event that said catheter is pulled into the urethra, whereby the balloon will be automatically deflated. In another embodiment, the retaining means comprises a plurality of coiled, flexible retaining fingers which extend longitudinally through the catheter to a slideable collar. The collar may be moved axially along the catheter to either advance the fingers outwardly therefrom or withdraw the fingers completely into the catheter. In yet another embodiment, the retaining means comprises a plurality of coiled, flexible, fluid filled retaining fingers which are inflated by way of fluid passages which extend longitudinally through the catheter. The coiled fingers will be automatically straightened should the catheter be pulled through the urethra. In an additional embodiment, the retaining means comprises a flexible, conical retaining skirt that is attached to the catheter along a peripheral hinge. The locking skirt is adapted to rotate around the hinge to a location over and above the catheter should the catheter be pulled into the urethra.

BRIEF DESCRIPTION OF THE DRAWINGS

FIG. 1 is a partial cross-section of the improved catheter according to one embodiment of the present invention;

FIG. 2 is a cross-section taken lines 2—2 of FIG. 1;

FIG. 3 is a cross-section taken along lines 3—3 of FIG. 1;

FIG. 7 is a partial cross-section of the improved catheter according to another embodiment of the present invention having a plurality of retaining fingers advanced outwardly from said catheter;

FIG. 8 is a cross-section taken along lines 8—8 of FIG. 7;

FIGS. 9–11 illustrate the improve catheter according to another embodiment of the present invention having a plurality of fluid filled fingers for retaining the catheter within the bladder;

DESCRIPTION OF THE PREFERRED EMBODIMENT

Figure 4:
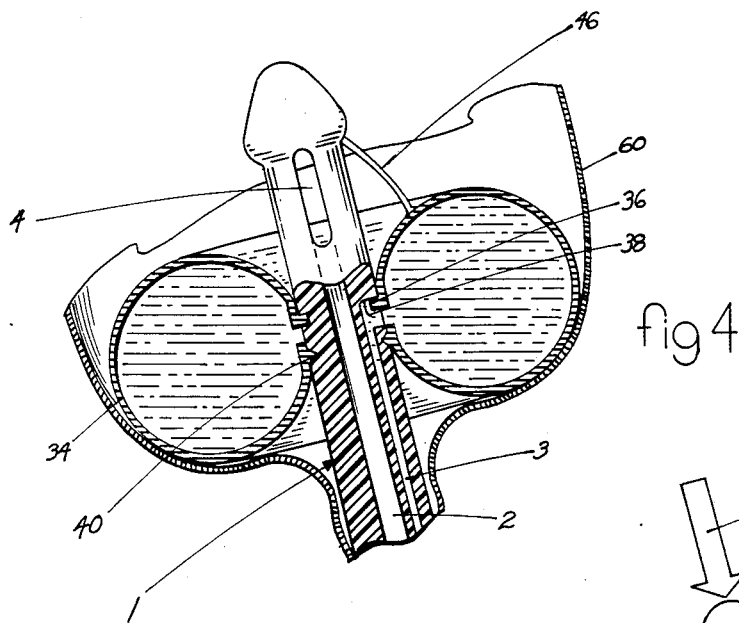
FIGS. 4–6 are partial cross-sections showing the structure and operation of an inflatable retaining balloon which may be deflated by separating the balloon from the catheter.

The improved urinary catheter 1 which forms the present invention is now described while referring concurrently to FIGS. 1-3 of the drawings. In FIG. 1, the catheter 1 is shown including a conventional Foley-style retaining balloon 50 which is received within the patient's bladder 60. Balloon 50 is inflated, while in situ, so as to be seated against the relatively narrow neck of a bladder 60, whereby to prevent an inadvertent removal of the catheter therefrom. The balloon 50 is inflated with a supply of fluid (e.g. water or isotonic or iso-osmotic fluid, or the like) via an inflation channel 3 which extends longitudinally through catheter 1 between the balloon 50 and a syringe docking port 5 having a check valve 7 associated therewith to prevent an inadvertent deflation of the balloon. As in a conventional catheter, the presently disclosed catheter 1 also includes a centrally disposed urine passage 2 which extends longitudinally through the catheter from a urine inlet aperture 4 to the distal base 6 at which urine can be collected in a bladder bag (not shown) for disposal.

Unlike the conventional catheters, and as an important feature of the catheter 1, an inflatable (e.g. latex) paraurethral torroid or balloon 8 is disposed within the urine passage 2. While the balloon 8 is shown located at the approximate mid-point of urine passage 8, it is to be understood that balloon 8 can be adjusted to slide distally or proximally along passage 2 to fit males or females of various anatomical configurations and different chronological ages. In the inflated condition (as illustrated in FIG. 1), torroidal balloon 8 extends across and occludes the urine passage 2 so as to block the flow of urine from inlet aperture 4 to distal base 6. Hence, and as will soom become apparent, the torroidal balloon 8 can be selectively inflated or deflated, whereby to function as a hydraulic valve for controlling the flow of urine through urine passage 2. Therefore, the catheter 1 may also have utility as a temporary artificial sphincter which may be removably implanted in an incontinient patient without requiring a surgical procedure.

The torroidal balloon 8 is inflated with a supply of fluid 10 (e.g. isotonic or iso-osmotic fluid) for a compressible, manually activatable fluid reservoir 12. More particularly, reservoir 12 is connected to a fluid tube 14 by way of a check valve 16 which has a pair of lobes that engage one another in a normally closed condition. Fluid tube 14 communicates with an inflation passage 18 which extends longitudinally through catheter 1 between torroidal balloon 8 and an additional inflatable torroidal balloon 20 that is located within urine passage 2 at the distal base 6 of catheter 1. In order to inflate the torroidal balloons 8 and 20, equal and opposite compressive forces are manually applied to reservoir 12. The hydrostatic pressure which is generated when reservoir 12 is compressed causes the lobes of check valve 16 to separate to permit fluid 10 to be supplied to inflation passage 18 via fluid tube 14. Inflation passage 18 delivers fluid to each of the balloons 8 and 20, whereupon said balloons are simultaneously inflated to form a redundant closure means which occludes the urine passage 2 and holds the patient continent. Releasing the reservoir 12 removes the hydrostatic pressure therewithin and permits check valve 16 to automatically return to its normally closed configuration, so as to block the return of fluid to the reservoir and prevent the deflation of balloons 8 and 30.

The inflation of the paraurethral torroidal balloon 8 causes a localized expansion of the catheter 1 against the patient's urethra so that a tensile force is exerted upon the urethral mucosa. Paraurethral torroidal balloon 8 may be reinforced to limit the expansion thereof to prevent tearing or ischemia of the urethral mucosa. Accordingly, the catheter 1 is efficiently and reliably sealed to the urethra 22 to prevent the undesirable flow of urine therebetween. The simultaneous inflation of torroidal balloon 20 at the distal base 6 of catheter 1 automatically closes the distal end of the catheter to reduce internal contamination which may result in urinary tract infection. That is to say, the void established within urine passage 2 between the pair of inflated balloons 8 and 20 prevents the reflux of contamination at the distal catheter base 6, whereby to inhibit the ascent of infection into the bladder 60.

When it is desirably to shrink the balloons 8 and 30 to open passage 2 to urine flow, equal and opposite compressive forces are manually applied to check valve 16, whereby to separate the lobes thereof and open said valve to fluid flow. Accordingly, fluid 10 is drained out of balloons 8 and 30 and returned to reservoir 12 via inflation passage 18 and fluid tube 14. While the balloons 8 and 30 are preferably inflated by a fluid, such as isotonic or iso-osmotic fluid, it is also within the scope of this invention to inflate balloons 8 and 30 with air. Therefore, the balloons 8 and 30 will shrink automatically over time (in approximately 12 hours) as the air permeates the latex material thereof. In this manner, the urine passage 2 is automatically opened in the event that both the patient and nurse forget to manually deflate the balloons 8 and 30.

The catheter 1 is also provided with a plurality of flushing ports 24. Each flushing port 24 communicates with a flushing channel 26 (best shown in FIGS. 2 and 3). Flushing channels 26 extend longitudinally through the catheter 1 between respective flushing ports 24 and an infusion part 28 located at the distal base 6. A suitable antiseptic or anti-bacterial fluid may be supplied to infusion port 28 (by means of a hypodermic syringe 30) for delivery to the flushing ports 24 via flushing channels 26. Accordingly, the antiseptic fluid is explused from each of the flushing ports 24 to reduce the possibility of urinary tract infection around the catheter 1.

Figure 5:
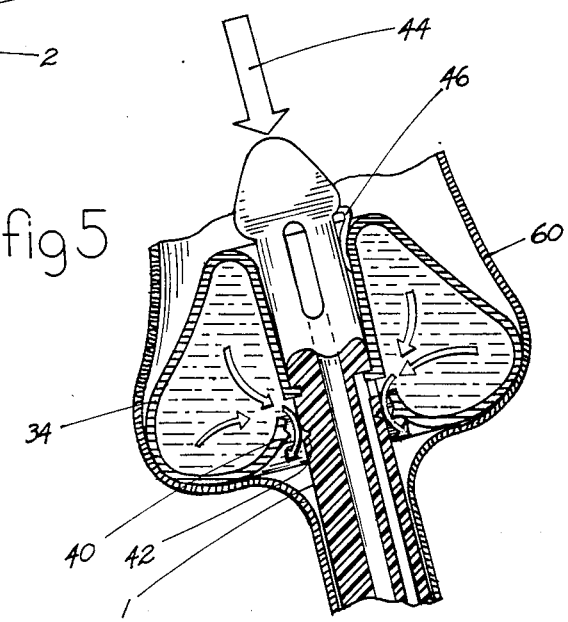
Figure 6:
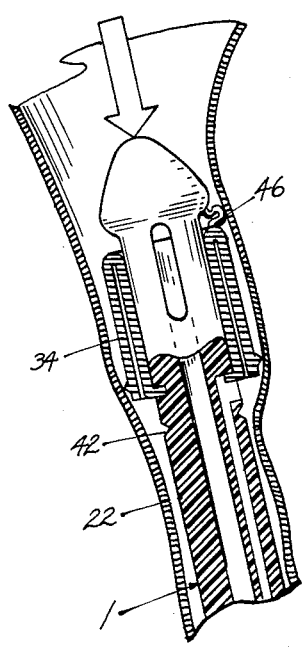

Referring now to FIGS. 4-6 of the drawings, the catheter 1 of FIG. 1 is shown with the conventional Foley-style balloon (designated 50 in FIG. 1) replaced by an improved torroidal (rather than a spherical) retaining balloon 34. As was earlier described, some patients pull out their catheters before the balloon has been properly deflated. The sudden removal of the catheter from the patient's urinary tract with the inflated Foley-style balloon retained within the bladder has been known to cause significant damage to the patient's internal organs which, in some cases, has been known to cause death. The retaining balloon 34 of the present embodiment overcomes the foregoing problem and reduces the likelihood of serious injury in the event that the catheter is unexpectedly pulled out by the patient.

More particularly, a top layer of the balloon 34 includes an edge 36 which is snap-fit within a catch 38 that extends around the periphery of catheter 1. A lower layer of the balloon 34 includes a detent 40 which is detachably received within a recess 42 that also extends around the periphery of catheter 1. As is best shown in FIG. 4, the balloon 34 is inflated, while in situ, with a supply of fluid via the longitudinally extending inflation channel 3. The balloon 34 is seated against the bladder 60 of the patient to retain catheter 1 therewithin so that urine can be collected in the usual manner through urine inlet aperture 4 and urine passage 2.

In the event that the patient should attempt to pull out the catheter 1 (in the direction of reference arrow 44 of FIG. 5), the inflated balloon 34 will be correspondingly pulled against the bottom of the bladder 60. Accordingly, the bottom layer of balloon 34 will be rotated slightly away from the catheter 1, whereupon to detach the detent 40 from its recess 42 (best shown in FIG. 5). The removal of detent 40 from recess 42 separates the balloon 34 from the catheter 1 and allows fluid to be expulsed, whereupon the balloon begins to shrink.

In FIG. 6, the balloon 34 is pulled through the patient's urethra 22 in a completely deflated condition. That is, the balloon 34 is compressed between the urethra 22 and the catheter 1, so that substantially all of the fluid is vented therefrom through the separation between the balloon and the catheter. Therefore, and unlike the Foley-style balloon of the conventional catheter, there is little resistance to oppose a pulling of the catheter 1 out of the bladder and through the urethra. Thus, the catheter 1 of FIGS. 4-6 may be pulled completely through the patient's urinary tract without imparting significant, and possibly life threatening, damage.

The balloon 34 is preferably tethered to the catheter 1 by means of a narrow flexible band 46. Accordingly, should the edge 36 of the balloon 34 be removed from its catch 38, whereby to completely detach the balloon from the catheter 1, the balloon will still remain connected to the catheter by the band 46. Therefore, the deflated balloon 34 can be removed through the patient's urinary tract along with the catheter 1 in the event that the catheter is pulled out by the patient.

Figure 14:
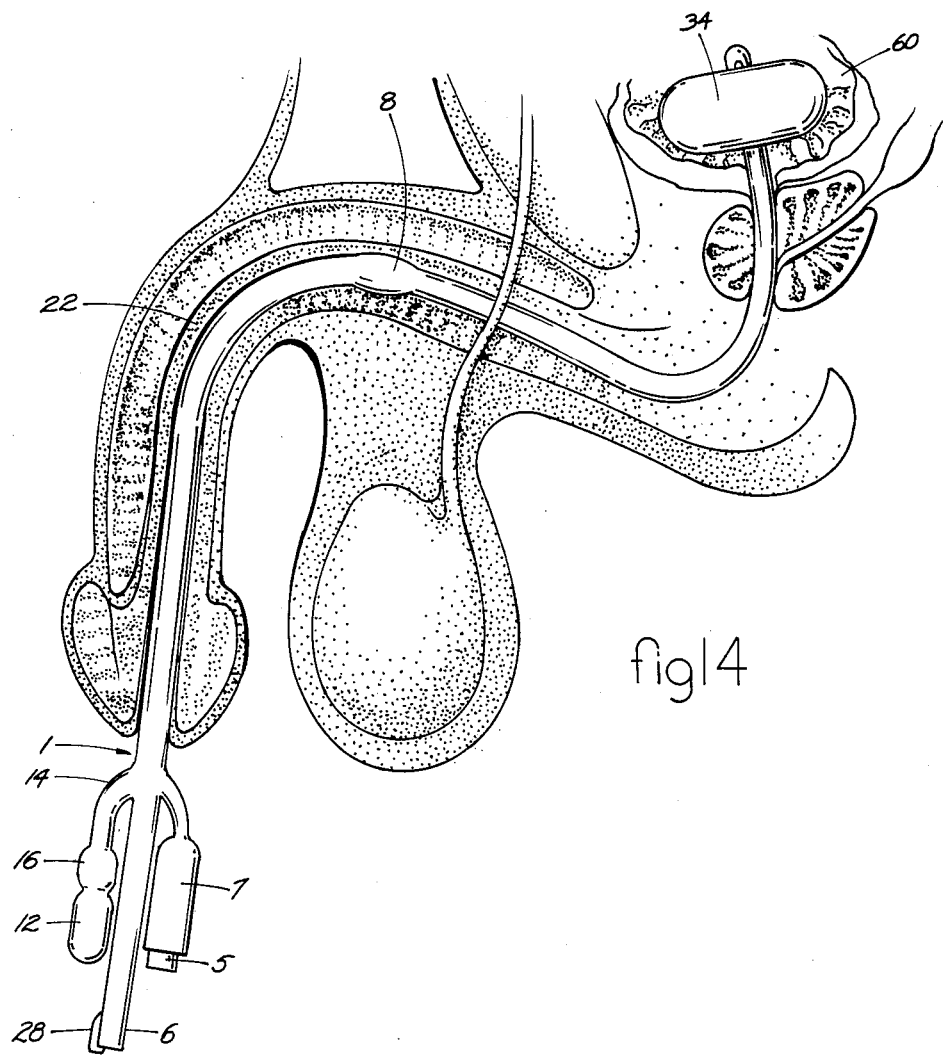
FIG. 14 is an anatomical illustration of the catheter of FIGS. 4–6 extending through the urinary tract of a male patient into the bladder.

FIG. 14 of the drawings is an anatomical drawing of a male patient showing the catheter 1 of FIGS. 4-6 extending through the urinary tract so that the torroidal balloon 34 may be inflated within the bladder 60.

In FIGS. 7 and 8 of the drawings, the Foley-style retaining balloon of FIG. 1 is completely eliminated from the catheter. The balloon is replaced by a plurality of coiled, flexible retaining fingers 52 (best shown in FIG. 7). The retaining fingers 52 are formed from a biocompatible, resilient material, such as silicone, or the like. As is best shown in FIG. 8, the retaining fingers 52 are of solid cross-section and extend longitudinally through the catheter 1 for connection to a lower collar 54. The lower collar 54 surrounds the catheter 1 and is slideable proximally and distally therealong, whereby the retaining fingers 52 are either advanced outwardly from or withdrawn into the catheter. (The lower collar is shown in phantom and designated by the reference numeral 54-1 in the distally oriented position, whereby the retaining fingers 52 would be withdrawn completely into the catheter 1). An upper fixed collar 56 also surrounds the catheter 1 and provides a convenient area at which to grip the catheter at which time that the lower collar 54 is moved proximally or distally for advancing or withdrawing the retaining fingers.

When the catheter 1 is received within the bladder, the lower collar 54 is moved proximally to advance the retaining fingers 52 outwardly from the catheter. The fingers are seated upon the bladder to retain the catheter therewithin. The fingers assume a torroidal (rather than a spherical) configuration, but consume a much smaller volume within the bladder than a Foley-style balloon. Urine may then be removed from the bladder in the normal fashion through the urine inlet aperture 4 and urine passage 2. However, should the patient suddenly attempt to pull out the catheter with the retaining fingers advanced outwardly thereof, the retaining fingers will be correspondingly pulled toward the bottom of the bladder. By virtue of the resilient nature thereof, the normally coiled fingers 56 will extend proximately (in the direction shown in FIG. 11) when the catheter is pulled through the patient's urethra. Hence, the retaining fingers 52 automatically yield or straighten in response to the force which is exerted thereon by the urethra, whereby to offer little resistance to the removal of the catheter. Thus, the catheter 1 of FIGS. 7 and 8 may be pulled completely through the patient's urinary tract without imparting significant damage.

As previously disclosed, the retaining fingers 52 of the catheter of FIGS. 7 and 8 are characterized by a solid cross-section. In FIGS. 9-11 of the drawings, the flexible retaining fingers 52-1 are provided with a partially hollow cross-section. Respective fluid passages 58 extend longitudinally through the catheter from each of the fingers 52-1. The passages 58 are filled with an isotonic or an iso-osmotic fluid, or the like, in a manner similar to that which was previously described for inflating the Foley-style balloon 50 of FIG. 1. Inflating each of the retaining fingers 52-1 with fluid maximizes the deflective resistance thereof.

Also extending through each finger 52 is a flexible metallic (e.g. stainless steel) strip 62. The strips 62 provide a relatively rigid support to pre-stress the fingers and preserve the torroidal configuration thereof so as to assure that the catheter will be adequately retained within the bladder 60. However, like the fingers 62 of FIGS. 7 and 8, fingers 62-1 will extend proximately should the patient suddenly pull the catheter from his bladder 60. Hence, by virtue of the flexible nature thereof, the normally coiled, fluid filled retaining fingers 62-1 of FIGS. 9-11 will automatically straighten in response to the force exerted thereon by the urethra 22 so as to offer little resistance to the removal of the catheter through the urinary tract.

Figure 12:
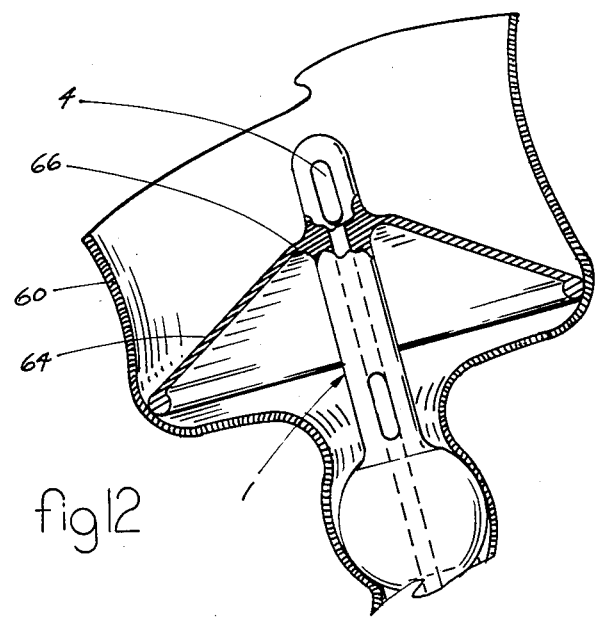
FIGS. 12–13 illustrate the improved catheter according to another embodiment of the present invention a rotatable, conical retaining skirt for retaining the catheter within the bladder.
Figure 13:
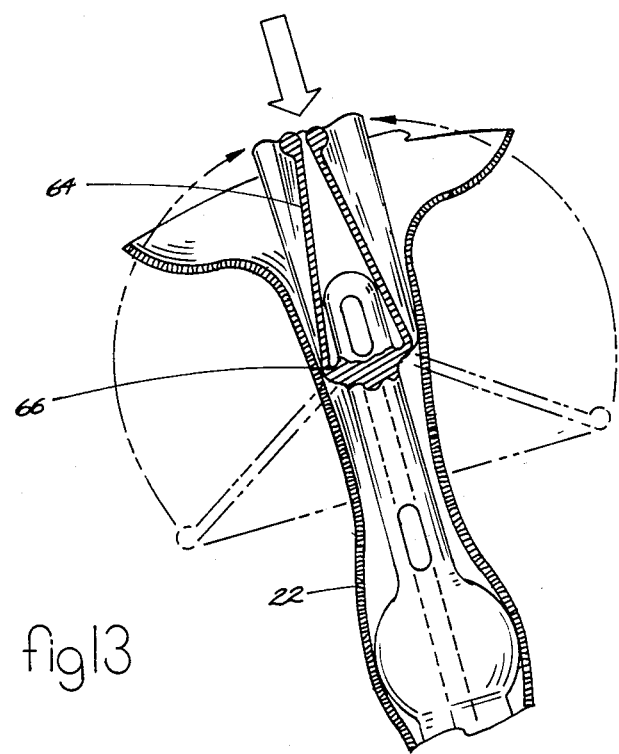

In FIGS. 12 and 13 of the drawings, the Foley-style balloon is replaced by a conical retaining skirt 64. Retaining skirt 64 is fabricated from a flexible, biocompatible material such as silicone, or the like. The retaining skirt is coextensively connected to the catheter 1 at a peripheral hinge or joint 66 around which the skirt may pivot. When the catheter 1 is received within the bladder 60, the retaining skirt 64 is distally biased to be seated upon the bladder for retaining the catheter therewithin. Urine may then be removed from the bladder through urine inlet apertrure 4 and the urine passage. In the event that the patient should attempt to forceably remove the catheter, the retaining skirt 64 will be correspondingly pulled into the urethra 22, and, by virtue of the flexible nature thereof, pivot around the hinge 66. Hence, and as is best shown in FIG. 13, retaining skirt 64 will be automatically rotated so as to extend proximally from hinge 66 to a location over and above the catheter at which to offer little resistance to the removal of the catheter through the patient's urinary tract.

As should now be apparent, each of the torroidal retaining means illustrated in FIGS. 4-13 of the drawings consumes less volume in the bladder than that which would ordinarily be consumed by a conventional, spherically shaped Foley balloon. Accordingly, both the frequency and severity of urinary bladder spasms, as commonly induced by the application of excessive pressure, such as that generated when a Foley balloon engages the trigonal area of the bladder, can be reduced. By eliminating the application of such pressure against the trigone, the patient will be less likely to experience a feeling of urgency when, in fact, no such urgency exists.

Figures 15, 16:
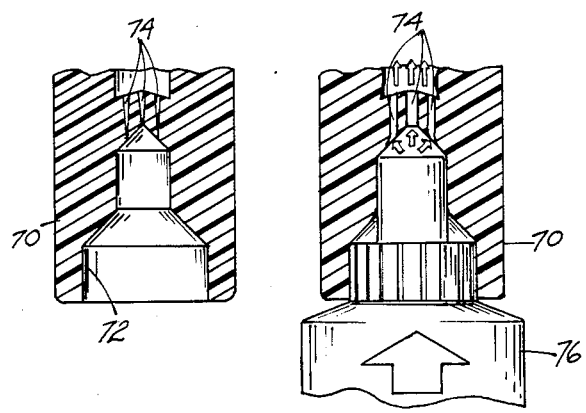
FIGS. 15 and 16 illustrate a unique check valve arrangement by which to control flow of fluid for inflating an inflatable catheter retaining device of the present invention.

FIGS. 15 and 16 of the drawings illustrate a unique check valve 70 which may substituted or the conventional Foley check valve 7 and docking port 5 shown in FIG. 1. Check valve 70 is fabricated from a resilient material, such as silicone, or the like, and has a hollow, molded interior 72, the shape of which conforms to the outline of the distal end of a hypodermic syringe (designated 76 in FIG. 16). However, the diameter of the hollow interior 72 of check valve 70 is slightly less than the corresponding diameter of syringe 76. Check valve 70 includes a plurality of normally closed fluid orifices 74. When a relatively wide fluid filled syringe 76 is located within the relatively narrow interior 72 of check valve 70, the valve 70 is stretched, whereby to open the fluid orifices 74. Accordingly, fluid may be inflused from syringe 76 into the inflation channel (designated 3 in FIG. 1) so that a retaining balloon (e.g. 50) may be inflated (or deflated) within the patient's bladder. Of course, when the syringe 76 is removed from the valve 70, the fluid orifices 74 automtically return to their normally closed condition.

It will be apparent that while a preferred embodiment of the invention has been shown and described, various modifications and changes may be made without departing from the true spirit and scope of the invention.

Having thus set forth a preferred embodiment of the invention, what is claimed is:

1. A urinary catheter to be extended through the urethra of a paitent for receipt within the bladder, said catheter comprising a urine passage extending longitudinally therethrough for removing urine from the bladder, means for retaining said catheter within the bladder, and first valve means communicating with said urine passage for controlling the flow of urine therethrough, said first valve means including an inflatable balloon surrounding said urine passage such that an inflation of said balloon occludes said urine passage and prevents the flow of urine therethrough.

2. The catheter recited in claim 1, further comprising a fluid delivery tube for delivering fluid to said inflatable balloon to inflate said balloon to thereby occlude said urine passage and prevent the flow of urine therethrough.

3. The catheter recited in claim 2, further comprising fluid source means communicating with said fluid delivery tube so that fluid can be delivered from said source means to said inflatable balloon said fluid source means comprising a compressible fluid filled reservoir.

4. The catheter recited in claim 3, further comprising a check valve located between said fluid source means and said fluid delivery tube to control the flow of fluid therebetween.

5. The catheter recited in claim 1, further comprising second value means communicating with said urine passage and spaced distally from said first valve means, said second valve means operating to close said urine passage and thereby inhibit the ascent of infection through said urine passage and into the bladder.

6. The catheter recited in claim 1, further comprising a plurality of flushing ports extending radially through said catheter from the interior to the exterior thereof and a corresponding plurality of flushing channels communicating with respective flushing ports and extending longitudinally through said catheter to supply an anti-bacterial material to said ports to be expulsed therefrom for reducing the possibility of urinary tract infection around the exterior of said catheter.

7. The catheter recited in claim 1, wherein said catheter retaining means is an additional inflatable balloon, said catheter further comprising an inflation channel communicating with said additional balloon and extending longitudinally through said catheter for delivering fluid to and thereby inflating said additional balloon, and a check valve to control the flow of fluid into said inflation channel, said check valve having a hollow, resilient valve body including at least one normally closed fluid orifice, the receipt of a fluid filled hypodermic syringe within said hollow body automatically opening said fluid orifice and permitting fluid to flow from said syringe to said additional balloon via said inflation channel.

8. The catheter recited in claim 1, wherein said catheter retaining means is an additional inflatable balloon, said additional balloon being releasably attached to said catheter at a surface of said additional balloon, such that a withdrawal of said catheter from the bladder separates said additional balloon from said catheter at said surface of said additional balloon, whereby to automatically deflate an inflated balloon through said separation.

9. The catheter recited in claim 1, wherein said catheter retaining means comprises a plurality of flexible retaining fingers extending outwardly from said catheter for engaging the bladder.

10. The catheter recited in claim 9, wherein said retaining fingers are of hollow construction, said catheter further comprising means for delivering a supply of fluid of and, thereby, inflating said fingers.

11. The catheter recited in claim 9, further comprising a collar being slideable axially along said catheter, said retaining fingers extending longitudinally through said catheter for connection to said collar, said finger being advanced outwardly from or withdrawn into said catheter depending upon the direction in which said collar is moved along said catheter.

12. The catheter recited in claim 1, wherein said catheter retaining means comprises a conical skirt pivotally attached to said catheter at a peripheral hinge, such that a withdrawal of said catheter from the bladder causes said conical skirt to rotate around said hinge to a location over and above said catheter.

13. A urinary catheter to be extended through the urethra of a patient for receipt within the bladder, said catheter including a urine passage extending longitudinally therethrough for removing urine from the bladder, means for retaining said catheter within the bladder, and inflation means communicating with said retaining means, said retaining means comprising an inflatable body which is detachably connected to said catheter at a surface of said body so as to be inflated, while in situ, by said inflation means, such that a withdrawal of said catheter from the bladder separates said inflatable body from said catheter at the surface of said body, whereby to automatically deflate said inflatable body through said separation.

14. The urinary catheter recited in claim 13, wherein said inflatable body is a balloon.

15. The urinary catheter recited in claim 13, wherein the surface of said inflatable body which is detachably connected to said catheter includes a detent and said catheter includes a recess, said detent being removably received within said recess for detachably connecting said inflatable body to said catheter.

16. The urinary catheter recited in claim 13, wherein said inflation means includes an inflation channel extending longitudinally through said catheter and communicating with said inflatable body for supplying fluid thereto.

17. The urinary catheter recited in claim 16, further including valve means communicating with said inflation channel to control the supply of fluid through said channel to inflate said inflatable body, said valve means having a hollow, resilient body and a resilient, normally closed orifice, the receipt of a syringe within the resilient body of said valve means deforming said valve means and thereby opening said resilient, normally closed orifice to permit communication between said syringe and said fluid channel via said orifice.

18. The urinary catheter recited in claim 13, wherein said inflatable body has a torroidal configuration which completely surrounds said catheter.

19. The urinary catheter recited in claim 13, further including means by which to tether said inflatable body to said catheter, whereby said inflatable body is withdrawn from the bladder with said catheter after said body has been separated from said catheter and deflated.

20. The urinary catheter recited in claim 13, further including inflatable valve means surrounding said urine passage and means to inflate said valve means, such that an inflation of said valve means occludes said urine passage and prevents the flow of urine therethrough.

* * * * *